US008552338B2

(12) United States Patent
Sercel et al.

(10) Patent No.: US 8,552,338 B2
(45) Date of Patent: Oct. 8, 2013

(54) SYSTEM AND METHOD FOR LASER MACHINING OF THREE-DIMENSIONAL STRUCTURES

(75) Inventors: Patrick J. Sercel, Brentwood, NH (US); Jeffrey P. Sercel, Hollis, NH (US)

(73) Assignee: IPG Microsystems LLC, Manchester, NH (US)

( * ) Notice: Subject to any disclaimer, the term of this patent is extended or adjusted under 35 U.S.C. 154(b) by 1352 days.

(21) Appl. No.: 12/125,439

(22) Filed: May 22, 2008
(Under 37 CFR 1.47)

(65) Prior Publication Data
US 2009/0127240 A1 May 21, 2009

Related U.S. Application Data

(63) Continuation of application No. PCT/US2006/045219, filed on Nov. 22, 2006.

(60) Provisional application No. 60/738,954, filed on Nov. 22, 2005.

(51) Int. Cl.
*B23K 26/08* (2006.01)
*B23K 26/38* (2006.01)
*A61F 2/02* (2006.01)

(52) U.S. Cl.
USPC ............ 219/121.69; 219/121.61; 219/121.82; 250/492.22; 264/400

(58) Field of Classification Search
USPC .......................... 219/121.85, 121.61, 121.82, 219/121.67–121.72; 430/269, 300, 307; 425/174.4; 264/400; 250/492.22, 250/503.1; 378/34
See application file for complete search history.

(56) References Cited

U.S. PATENT DOCUMENTS 3,422,246 A * 1/1969 Wetzel ..................... 219/121.67
4,504,354 A * 3/1985 George et al. ................. 216/10
4,507,535 A * 3/1985 Bennett et al. ........... 219/121.71
(Continued)

FOREIGN PATENT DOCUMENTS

JP           57094482        6/1982
JP           07323387       12/1995
JP        2001162392 A  *   6/2001

OTHER PUBLICATIONS

International Search Report and Written Opinion dated Apr. 19, 2007 issued in International Patent Application No. PCT/US06/45219.

*Primary Examiner* — Samuel M Heinrich
(74) *Attorney, Agent, or Firm* — Grossman Tucker Perreault & Pfleger, PLLC

(57) ABSTRACT

A system and method of laser machining rotates a workpiece about an axis of rotation, and translates the workpiece in a first direction along the axis of rotation. A mask defining a shape is translated in a second direction opposite the first direction, and a laser beam is directed at the mask such that the laser beam is scanned across the mask and at least a portion of the laser beam passes through the mask and toward the workpiece. The mask and the workpiece are translated with coordinating opposing motion to cause the laser beam to be imaged onto the workpiece with a shape or pattern corresponding to a shape or pattern defined by the mask. Rotation of the workpiece and the shape of the image on the workpiece produce different vectorial intensities such that material of the workpiece is removed to different respective depths to form a three-dimensional structure.

11 Claims, 6 Drawing Sheets

(56) References Cited

U.S. PATENT DOCUMENTS

| | | | |
|---|---|---|---|
| 4,734,729 A * | 3/1988 | Hertzel et al. | 396/584 |
| 4,784,135 A | 11/1988 | Blum et al. | |
| 5,160,823 A | 11/1992 | Bennin et al. | |
| 5,770,123 A * | 6/1998 | Hatakeyama et al. | 264/1.21 |
| 5,906,608 A * | 5/1999 | Sumiya et al. | 606/5 |
| 5,912,469 A * | 6/1999 | Okino | 250/492.23 |
| 5,948,292 A * | 9/1999 | Tanaka et al. | 219/121.82 |
| 6,086,773 A * | 7/2000 | Dufresne et al. | 216/8 |
| 6,160,240 A | 12/2000 | Momma et al. | |
| 6,521,865 B1 * | 2/2003 | Jones et al. | 219/121.72 |
| 6,534,741 B2 * | 3/2003 | Presby | 219/121.69 |
| 6,574,024 B1 * | 6/2003 | Liu | 359/220.1 |
| 6,888,987 B2 * | 5/2005 | Sercel et al. | 385/39 |
| 7,072,566 B2 * | 7/2006 | Seo et al. | 385/147 |
| 8,278,590 B2 * | 10/2012 | Hall et al. | 219/121.69 |
| 2002/0193866 A1 | 12/2002 | Saunders | |
| 2003/0087024 A1 | 5/2003 | Flanagan | |
| 2007/0017908 A1 | 1/2007 | Sercel et al. | |

* cited by examiner

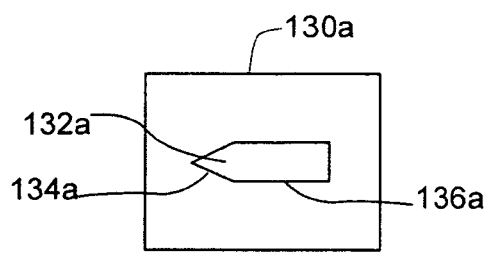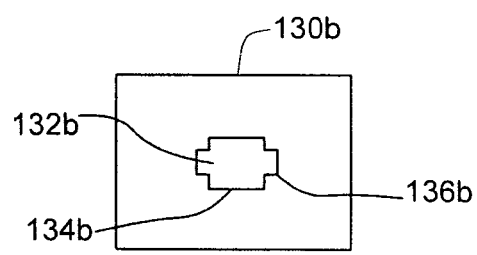
FIG. 3A　　　　　　　FIG. 4A
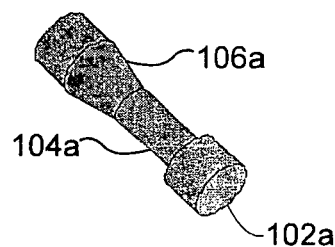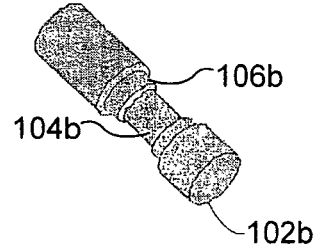
FIG. 3B　　　　　　　FIG. 4B

SYSTEM AND METHOD FOR LASER MACHINING OF THREE-DIMENSIONAL STRUCTURES

CROSS-REFERENCE TO RELATED APPLICATIONS

This application is a U.S. continuation of co-pending PCT Patent Application Serial No. PCT/US06/45219 filed Nov. 22, 2006 which claims the benefit of U.S. Provisional Patent Application Ser. No. 60/738,954, filed on Nov. 22, 2005, which is fully incorporated herein by reference.

TECHNICAL FIELD

The present invention relates to laser machining and more particularly, to a laser machining system and method capable of creating three-dimensional structures on a rotating workpiece.

BACKGROUND INFORMATION

Lasers have been used to perform cutting, etching, and other types of machining operations on various types of structures made of various types of materials. In particular, lasers can be used to micromachine complex patterns on structures. When a laser pulse hits a structure, the laser energy may cause material to be removed. A structure may be machined by using the laser to selectively remove material according to the desired pattern. The operating characteristics and parameters of the laser (e.g., wavelength, pulse rate, energy density) may be controlled to control the laser energy and thus the amount of material removed. Some structures, such as biomedical devices, may be difficult to machine using a laser because of the material and/or the shape of the structure.

In general, laser ablation is the removal of thin layers (usually sub micron) of material at low fluence levels, where the ablated material carries at least some of the residual heat away from the remaining workpiece. Fluence may be defined as energy density per laser pulse and energy density is generally defined as the intensity of an individual laser pulse focused onto a workpiece. The fluence multiplied by pulses per second is generally referred to as power density.

The ablation threshold is the practical energy density where detectable amounts of material begin to be removed. When the energy density is above the ablation threshold of a material, the material will be ejected and will carry away excess or residual heat energy. Below the ablation threshold, the laser energy is converted into heat within the material. As the ablation depth increases, the energy density threshold may increase and the residual heat penetration may increase (i.e. the laser energy transmitted into the depth of the material not ablated). In general, optimum fluence is the fluence level that provides the highest efficiency of material removal and the lowest percentage of residual heat left in the material after ablation. Excessive fluence is the higher range of fluences where the etch rate becomes saturated and excess energy is converted into heat in the remaining material adjacent to and below the etched or ablated volume.

Residual heat penetration during ablation may affect the resolution of the features that are machined. In general, high resolution is ability to generate fine features, for example, using laser ablation with little or no detectable melting as compared to the sizes of the features desired. Heat free or cool excimer laser ablation may use low energy densities to strip fine (e.g., sub-micron) layers with high resolution such that excess heat may be carried away primarily in the ablated materials and the residual heat left in the remaining materials is low enough to substantially eliminate melting.

Certain types of materials may be more difficult to machine with lasers than others. Sensitive materials are normally not easily processed at longer wavelengths (e.g., at 248 nm) due to optical and thermal effects. Sensitive materials generally have an optical absorption at the 248 nm wavelength that is low compared to the optical absorption at the 222 nm, 193 nm or 157 nm wavelengths. Sensitive material may also have a relatively low thermal capacity and/or low melting point, i.e., it will melt and deform with low heat input (or low power density). Examples of sensitive materials include, but are not limited to, polymers, other low density organic materials such as PMMA, collagen, living tissue such as the cornea, resorbable polymers, types of nylon, delrin, PET, Mylar and the like.

As an example, a sensitive material, such as PMMA, has an OAC of about 65 $cm^{-1}$ at 248 nm and about $2.0 \times 10^3$ $cm^{-1}$ at 193 nm, and also has a relatively low melting temperature. Using existing laser machining systems, PMMA may be effectively processed at 193 nm with good resolution at moderate power densities but may only be marginally processed at 248 nm. In contrast, a non-sensitive material that may be processed at 248 nm, such as polyimide, has an optical absorption coefficient (OAC) of about $2.8 \times 10^5$ $cm^{-1}$ at 248 nm and about $4.2 \times 10^5$ $cm^{-1}$ at 193 nm. Polyimide can be effectively processed, with little or no melting, at high repetition rates (i.e., >400 Hz) at 248 nm due to its strong absorption at that wavelength. Polyimide also has a relatively high melting temperature and can also withstand higher power densities.

When a laser is used to machine thermally sensitive polymers, the material surrounding the area being machined has a tendency to melt or deform under laser irradiation. During laser ablation, the low optical absorption coefficient (OAC) of the sensitive material results in a deeper penetration depth of the laser energy into the material and therefore a larger volume of material is removed with each laser pulse, which may require the laser fluence (i.e., energy density per laser pulse) to be higher. In other words, if the absorption depth of a material is relatively large (e.g., as compared to a heat free excimer laser processing condition), the energy density required to ablate the material also increases. The longer absorption depth coupled with the higher required ablation threshold energy density may result in a larger etch depth per laser pulse and may also result in a larger residual heat which consequently remains in the material adjacent to the etch zone after ablation.

To avoid damage or degradation due to thermal effects, therefore, some laser machining techniques have been carefully designed to use a specific wavelength and/or energy density that will minimize thermal effects. In some applications, for example, a wavelength of 193 nm is used to process sensitive materials, such as resorbable polymers, because of the stronger absorption at the shorter 193 nm wavelength. Machining using a 248 nm laser, however, has other advantages over a 193 nm laser. A 248 nm laser produces higher laser power for essentially the same cost as a 193 nm laser. The beam delivery system of a 248 nm laser may be less expensive due to the ability of 248 nm to be transmitted through air while a 193 nm laser may require a sealed and $N_2$ purged beam delivery system. The beam delivery optics for a 248 nm laser generally cost less and last longer than for 193 nm lasers. The operation cost of a 248 nm laser may also be lower due to a longer life of the laser resonator and beam splitter optics, the laser tube component and the laser gas fill and due to lower stress on high voltage components. The 248 nm laser may also be intrinsically more stabile in terms of power and energy fluctuations than the 193 nm laser.

Thus, a 248 nm laser may provide advantages in laser machining applications but may have drawbacks when used to machine sensitive materials. In particular, the achievable resolution may be limited due to the melting effects. Sensitive materials may be effectively processed using a 248 nm laser at low power density, (i.e., low laser pulse repetition rates) if the power density is low enough to allow time for the residual laser energy to dissipate within the material. However, this limits the effective processing speed for the sensitive materials and therefore limits the economics for high volume production applications.

Increased power density directly relates to material heating and therefore the melting and thermal effects generated during laser processing. Power density can be reduced, for example, by reducing the pulse repetition rate or by reducing the amount of time the material is exposed to the high repetition rate laser. Thus, a fast scanning speed of the workpiece under a laser beam can reduce the effective, local power density delivered to that workpiece. When using fast scanning speeds, however, the ability to image complex non-repeating features over a large area may be difficult due to the optics required to image a large area with high optical resolution. Machining complex patterns may be even more difficult on certain shapes, such as a curved surface on a cylindrical structure.

In addition to the challenges presented by certain materials, laser machining of certain types of structures has also presented problems. Using laser micromachining to create three-dimensional (3-D) structures on a curved surface, for example, has been difficult to achieve with existing systems and methods. In particular, when the size of a 3-D structure is over a few millimetres, conventional near field imaging from an excimer laser may not properly create the large structure due to its limited maximum field of view.

Accordingly, there is a need for a system and method for laser machining 3-D structures on a workpiece made of a variety of materials.

BRIEF DESCRIPTION OF THE DRAWINGS

These and other features and advantages will be better understood by reading the following detailed description, taken together with the drawings wherein:

FIG. 3A is a schematic diagram of one embodiment of a mask that may be used in the system for machining.

FIG. 3B is a perspective view of a workpiece machined using the mask shown in FIG. 3A.

FIG. 4A is a schematic diagram of another embodiment of a mask that may be used in the system for machining.

FIG. 4B is a perspective view of a workpiece machined using the mask shown in FIG. 4A.

DETAILED DESCRIPTION

Figure 1:
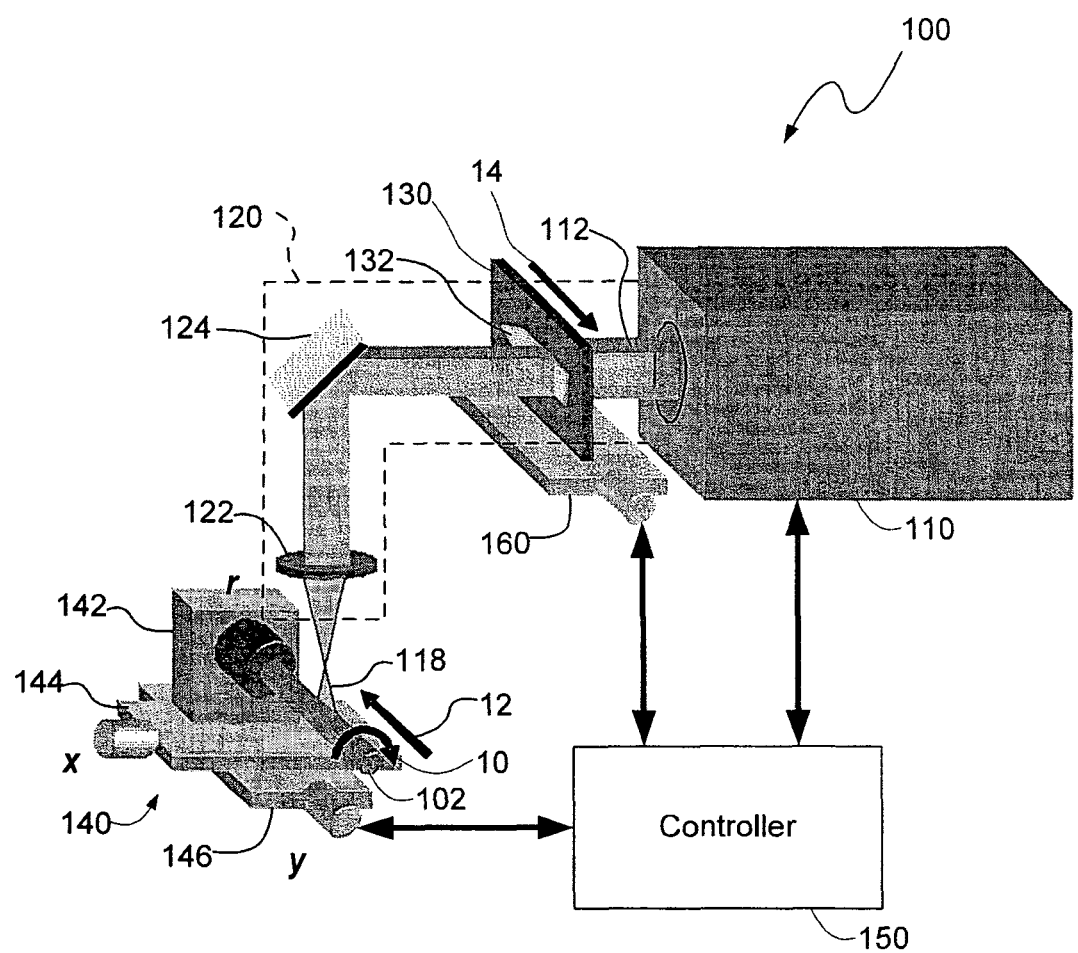
FIG. 1 is a schematic diagram of a system for machining, consistent with one embodiment of the present invention.

Referring to FIG. 1, a laser machining system 100, consistent with one embodiment of the present invention, may be used to machine a 3-D structure on a rotating workpiece 102. In the exemplary embodiment, the workpiece 102 is generally cylindrical or tubular in shape, although the system and method described herein may be used to machine other shapes. The 3-D structures that may be machined on the workpiece 102 include, but are not limited to, screw threads and hourglass shapes parts. Examples of the workpiece 102 include, but are not limited to, biomedical devices. The workpiece 102 may be made of sensitive materials, such as polymers, other low density organic materials such as PMMA, collagen, resorbable polymers, types of nylon, delrin, PET, Mylar and the like, or non-sensitive materials, such as such as polyamide.

The machining system 100 may include a laser 110 for generating a laser beam 112, a beam delivery system 120 for delivering and/or shaping the laser beam 112, a mask 130 for providing a shape or pattern to image the laser beam 112, and a workpiece holder 140 for holding and moving the workpiece 102 such that a surface of the workpiece 102 is in a path of the laser beam 112. A controller 150 may be coupled to the laser 110, the mask 130, and the workpiece holder 140 to control the operation of the laser 110 and the movement of the mask 130 and the workpiece 102. Although FIG. 1 shows one arrangement of the machining system 100, those skilled in the art will recognize other configurations and arrangements of the laser 110, the beam delivery system 120, the mask 130 and the workpiece holder 140.

According to a method of machining, the workpiece 102 may be rotated about its axis of rotation, as indicated by arrow 10, while being translated or moved linearly in a direction along the axis of rotation, as indicated by arrow 12. The mask 130 may be translated or moved linearly in a direction, as indicated by arrow 14, which is opposite the linear direction of the workpiece 102. Alternatively, the workpiece 102 and mask 130 may be rotated and/or translated in directions opposite that shown in the exemplary embodiment.

The laser beam 112 may be directed at the moving mask 130 such that the laser beam 112 is scanned across the mask 130 and at least a portion of the laser beam passes through the mask 130. The mask 130 and the workpiece 102 may be moved with coordinated opposing motion (COMO) to cause the laser beam 112 to be imaged onto the workpiece 102 with a shaped or patterned image 118 corresponding to the shape or pattern defined by the mask 130. The laser beam 112 may also be reduced or demagnified such that the shaped or patterned image 118 is imaged at a reduced ratio onto the workpiece 102. The coordinated motion of the mask 130 and the workpiece 102 may be based on a ratio related to the demagnification of the image on the workpiece 102. If the demagnification is five (5) times, for example, the mask 130 moves five (5) times faster than the workpiece 102 in the opposite direction.

The energy of the laser beam 112 imaged onto the workpiece 102 may cause removal of material as a result of ablation. The amount of material removed may depend upon the intensity of the laser beam 112 in contact with the surface of the rotating workpiece 102. The rotation of the workpiece 102 and the shape of the laser beam imaged on the workpiece 102 produces different vectorial intensities on the rotating workpiece 102 in the scanning direction (also referred to as a convolution of intensity). When the shape or pattern of the image 118 on the rotating workpiece 102 is wider in the direction of rotation, for example, the intensity is higher and more material is removed. As a result of the different vectorial intensities, the material of the rotating workpiece 102 may be removed to different respective depths, forming a 3-D structure corresponding to the shape or pattern of the laser beam image 118 on the workpiece 102. Thus, the shape or pattern defined by the mask 130 may be used to control the amount of ablation at the workpiece 102, which determines the shape of the 3-D structure.

The speed of rotation and/or the laser energy density may be varied to vary the depth of the material removed. The machining method advantageously allows workpieces having lengths longer than the width of the laser beam 112 to be continuously patterned and shaped without stitching effects. The length of the shape that may be continuously formed on a workpiece may be limited by the mask travel and the demagnification ratio.

According to one embodiment, the laser 110 may be a vacuum ultraviolet (VUV) excimer laser having a wavelength of 193 nm, and the beam delivery system 120 may be a sealed beam delivery system that has been purged with an inert UV transmitting gas such as argon or nitrogen ($N_2$). Alternatively, the laser 110 may be an excimer laser having longer wavelengths such as 157 nm or 248 nm. The laser 110 may also be configured for precision laser triggering, for example, using a fire on the fly technique. Those skilled in the art will recognize that other lasers and wavelengths may be used.

The beam delivery system 120 may include one or more imaging lenses 122 that provide the reduction or demagnification of the beam. The lenses 122 may provide demagnification in a range from less than 1× to greater than 10×. The reduction or demagnification facilitates the formation of smaller features with higher resolution on the workpiece 102. Those skilled in the art will recognize that other optical components may be used to provide reduction or demagnification of the beam. The beam delivery system 120 may also include one or more beam reflectors 124 that change the direction of the beam. The lens system employed in the beam delivery system 120 may be simple since the lens may always be used in the paraxial, on-axis condition.

Figure 2:
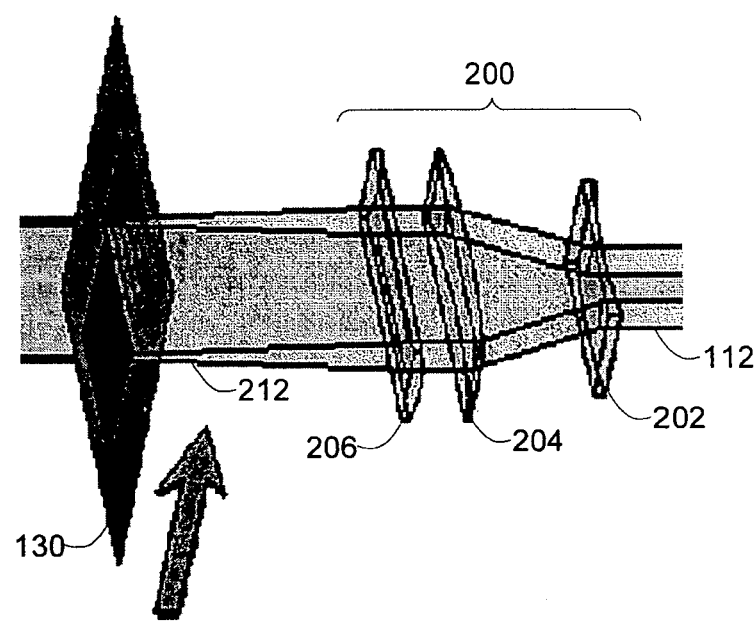
FIG. 2 is a schematic diagram of optics used in a beam delivery system, consistent with one embodiment of the present invention.

The beam delivery system 120 may further include optics (not shown in FIG. 1) between the excimer laser 110 and the mask 130, such as anomorphic optics, for providing a shaped beam, such as a long, narrow beam. According to one embodiment shown in FIG. 2, the optics 200 between the laser 110 and the mask 130 may include a cylindrical plano-concave lens 202 that expands the length of the raw beam 112 in one axis or direction, and a cylindrical plano-convex lens 204 that collimates the expanded beam in the same axis or direction. A cylindrical plano-convex lens 206 focuses the expanded beam and narrows the width of the beam in another axis or direction to produce a tightly focused line shaped beam 212. The beam may be expanded to have a length (i.e., in the long direction) that corresponds to the shape or pattern defined by the mask 130. The beam may be focused to have a width (i.e., in the narrow direction) that provides a desired effective power density. In one example, the length of the line shaped beam 212 may be in the range of about 20 mm to 35 mm, and preferably about 32 mm and the width of the line shaped beam 212 may be in the range of about 0.1 mm to 5 mm, and preferably about 1 mm. Those skilled in the art will recognize that other optical components and/or other configurations of optical components may also be used in the beam delivery system 120 to provide a tightly focused line shaped beam.

The beam delivery system 120 may also include optics to defocus the beam 112 during at least part of the machining process. For example, the beam may be defocused during the last pass of the COMO scanning to smooth the surface of the workpiece 102. This advantageously prevents edges of a sharply focused beam from leaving traces upon the spiral motion caused by the coordinated motion of the rotation and translation.

The mask 130 may be coupled to a mask stage 160, such as an air bearing or other high resolution and high accuracy motion system, which is configured to move the mask 130 in one or more axes. The mask 130 may include one or more apertures 132 defining the shape or pattern that causes the laser beam 112 to be imaged in a shape or pattern on the workpiece 102. The aperture 132 may be larger than the laser beam 112 from the laser 110. To image the entire area of the aperture 132 of the mask 130, the mask stage 160 may be used to translate the mask 130 such that the stationary laser beam 112 is scanned across the aperture 132. The movement of the mask 130 may be controlled such that the laser beam 112 exposes only the open areas or aperture 132 of the mask 130, resulting in high beam utilization efficiency. Alternatively, the mask 130 may be stationary and the laser 110 may be moved to scan across the mask 130.

The dimensions of the shape or pattern defined by the mask 130 controls the vectorial intensities of the laser beam 112 imaged on the workpiece 102 and thus corresponds to the shape of the 3-D structure created on the workpiece 102. The width of the aperture 132, for example, in a direction transverse to the direction of translation of the mask 130 corresponds to the width of the laser beam image 118 in the direction of rotation of the workpiece 102 and the depth of material removed.

FIG. 3A shows one embodiment of a mask 130a, and FIG. 3B shows one embodiment of a workpiece 102a machined using the mask 130a. This embodiment of the mask 130a includes an aperture 132a with a V-shaped portion 134a and a rectangular portion 136a. The V-shaped portion 133a creates a vectorial intensity that varies from the tip of the "V" to the wider portion of the "V," which causes an increasing amount of material to be removed from the tip to the wider portion of the "V." This forms a tapered portion 106a on the workpiece 102a. The rectangular portion 131a creates a substantially constant vectorial intensity on the workpiece 104, which forms an annular portion 104a having a substantially constant depth on the workpiece 102a.

FIG. 4A shows another embodiment of a mask 130b, and FIG. 4B shows one embodiment of a workpiece 102b machined using the mask 130b. This embodiment of the mask 130b includes an aperture 132b with a wider middle rectangular portion 134b and narrower outer rectangular portions 136b. Because each of the portions 134b, 136b has a substantially constant width, they create annular portions of substantially constant depth on the workpiece 102b. The wider middle rectangular portion 134b creates a deeper portion 104b and the narrower outer portions 136b create shallower portions, forming a stepped 3-D structure around the workpiece.

Those skilled in the art will recognize that the mask may define other shapes or patterns, such as a round shape to create parabolic shaped 3-D structures or a diamond shape to create a V-shaped 3-D structure. Although a single aperture is shown, a mask may include multiple apertures to create multiple 3-D structures in different locations on the workpiece.

The workpiece holder 140 may include an A-axis rotation stage 142 that supports the workpiece 102 and rotates the workpiece 102 about its axis of rotation. The workpiece holder 140 may also include one or more translation stages 144, 146 that translate the workpiece 102 in one or more linear directions, for example, along X and Y axes. The translation stages 144, 146 may include linear translation devices to move the stages and position encoders to monitor the position of the stages 144, 146. The A-axis rotation stage 142 may be mounted on one of the stages 144, 146. The A-axis rotation stage 142 may be used to continuously rotate the workpiece 102, while the Y-axis translation stage 146 translates the workpiece 102 in the axial direction to scan the workpiece 102 with the imaged beam. The X-axis translation stage 144 may be used to align the rotating workpiece 102 with the beam image 118, as described below.

Figure 5:
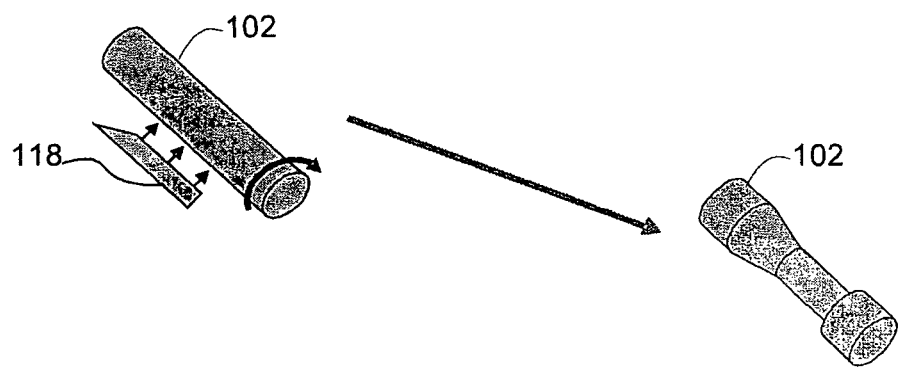
FIG. 5 is a schematic diagram of one method of machining using side processing, consistent with one embodiment of the present invention.

While the rotating workpiece 102 is translating in the Y axis direction, the laser beam 112 may be aligned to scan the radial direction of the rotating workpiece 102 to produce the convolution of intensity. The laser beam may be aligned differently for different processing methods used to create the convolution of intensity on the rotating workpiece 102. According to a side processing method, as shown in FIG. 5, the shaped or patterned laser beam image 118 may be aligned and side fed to the rotating workpiece 102, similar to a lathe. For example, the X axis translation stage 144 may be used to move the rotating workpiece 102 into the image 118 until the image 118 is directed at a tangential surface of the rotating workpiece 102.

Figure 6:
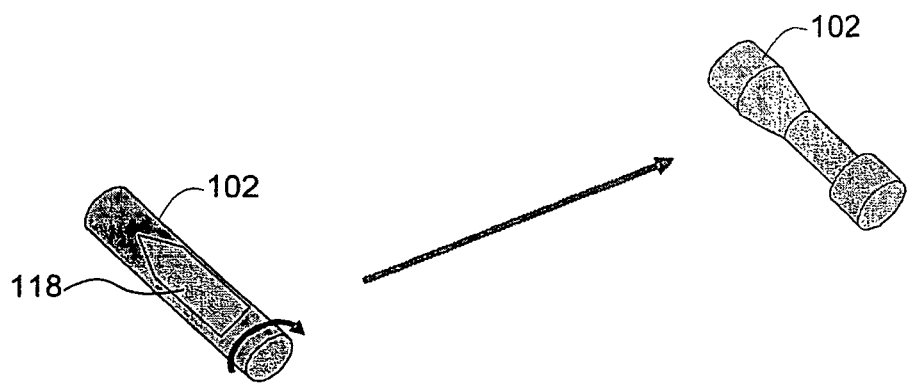
FIG. 6 is a schematic diagram of one method of machining using top processing, consistent with another embodiment of the present invention.
Figure 7B:
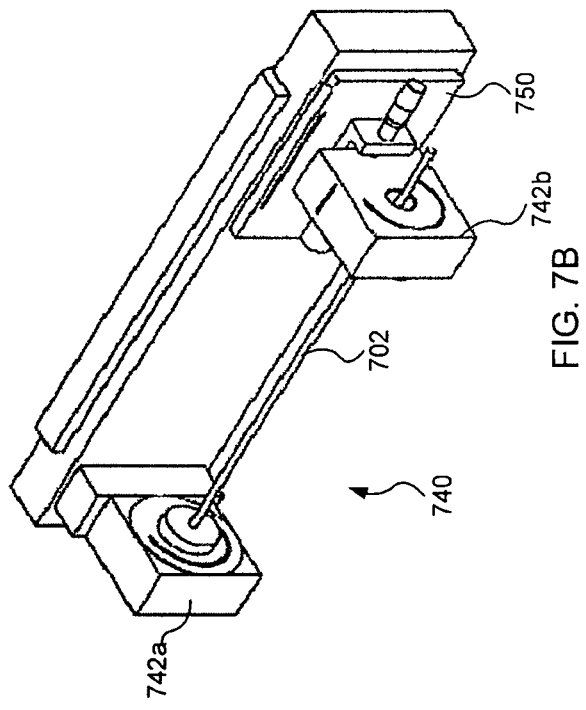
FIG. 7B is a perspective view of the workpiece holder shown in FIG. 7A.
Figure 7D:
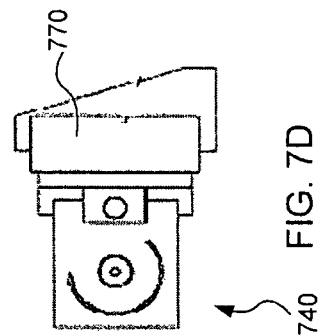
FIG. 7D is an end view of the workpiece holder shown in FIG. 7A.
Figure 7A:
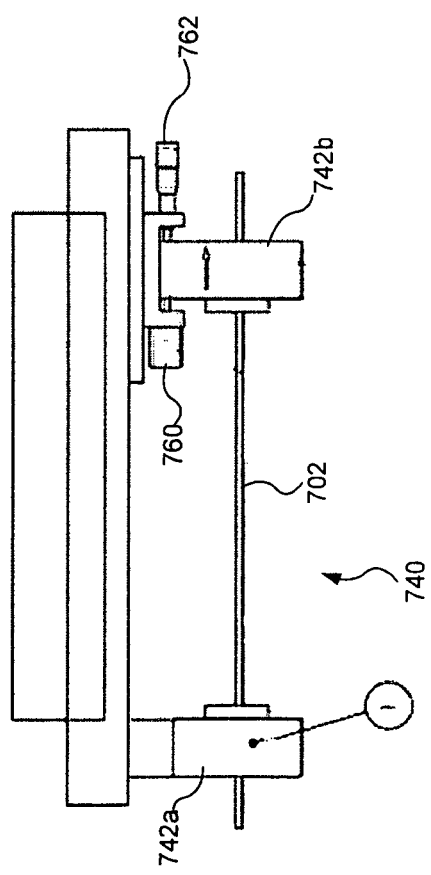
FIG. 7A is a side view of a workpiece holder, consistent with one embodiment of the present invention.
Figure 7C:
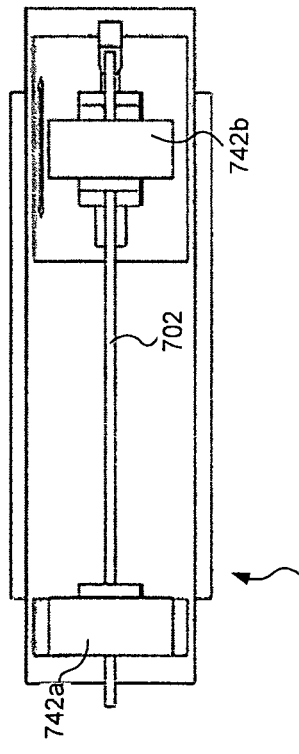
FIG. 7C is a top view of the workpiece holder shown in FIG. 7A.

According to a top processing method, as shown in FIG. 6, the shaped or patterned laser beam image 118 is directed onto the top surface at normal incidence to the rotating workpiece 102. The top processing method may be advantageous because the laser beam image 118 is stationary on the rotating part and does not require precise alignment to feed the beam. Also, the top processing method may use two-fold symmetry of the shaped or patterned image 118 on the rotating workpiece 102, which doubles the size of the illuminated area and reduces processing time. The top processing method may also reduce processing errors due to the workpiece rotation run out because the run out of the workpiece is effectively translated into the Z axis beam direction where the depth of field of the imaging lens has a greater value.

Referring to FIGS. 7A-7D, another embodiment of a workpiece holder 740 may include two rotation stages with workpiece supports supporting each end of the workpiece 702. One rotation stage 742b may be slaved in motion to the other rotation stage 742a to rotate the workpiece 702 with minimal or no rotational torque transferred to the workpiece 702. One of the workpiece supports may be a movable tailstock support 750 to allow workpieces of various lengths to be properly supported between the rotation stages 742a, 742b. The gripping area of the workpiece supports may be located near the processing zone. The workpiece holder 740 may also include a tensioning device 760, 762 that places the workpiece 702 under tension to straighten the workpiece during high accuracy processing. One example of the workpiece tensioning device 760, 762 includes an air cylinder 760 that adds a small movement to tighten up the tension in the workpiece 702 after it is mounted and a precision micrometer 762 that controls the stroke of the air cylinder 760.

The workpiece holder may also include an integrated Z axis stage 770 that moves the entire assembly up and down as a unit. The Z axis stage 770 may use a driven Z wedge crossed roller stage located to the side of the dual rotation stages 742a, 742b. The rotation stages 742a, 742b may be mounted with a low profile to hold the workpiece near the translation stages for improved tracking to the translation stage position encoders.

Figure 8B:
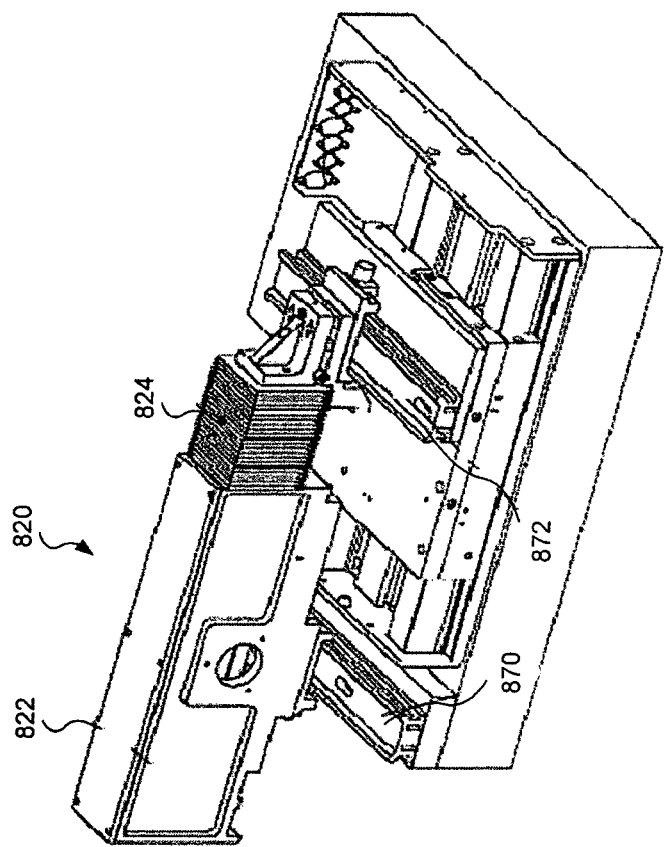
FIGS. 8A and 8B are perspective views of a beam delivery system, consistent with one embodiment of the present invention.
Figure 8A:
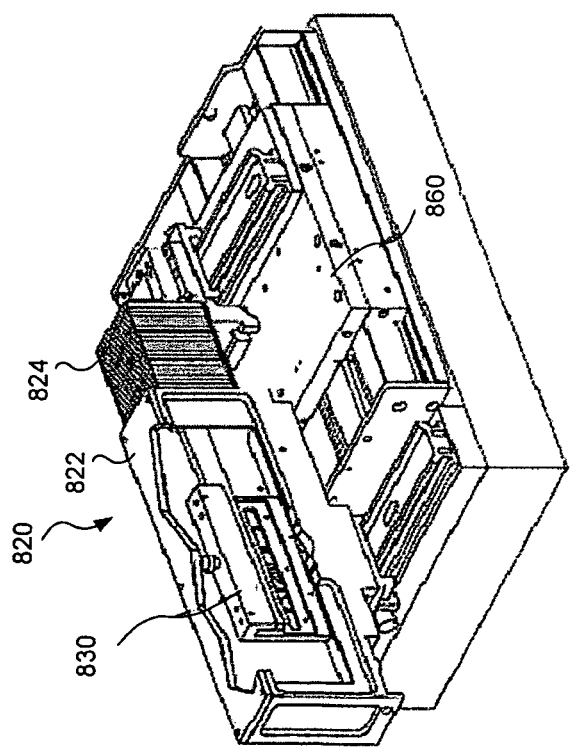

Referring to FIGS. 8A and 8B, another embodiment of a beam delivery system 820 may include an integrated mask 830 and mask stage 860. The mask 830 may be located within the sealed and purged environment 822 (e.g., a gas tight box) of the beam delivery system 820. The mask stage 860 may be coupled to the mask 830 in a manner that allows environmentally isolated movement of the mask 830 while the mask stage 860 remains located outside of the sealed environment. In one embodiment, the mask 830 may be supported by a support rod mounted to the mask stage 860. The beam delivery system 820 may include dove tail rails 870, 872 that allow movement of the purged environment 822 along the beam direction. One rail 870 may be fixed to the purged environment 822 and the other rail 872 may be mounted on the stage 860 to hold the moving mask 830 to the stage 860. The support rod may be sealed using a linear movable seal 824. Examples of a linear movable seal include a bellows of metal or flexible material and a shaft seal such as a spring energized Teflon wiper type seal.

The controller may include a computer programmed with software, as is generally known to those skilled in the art. The controller 150 may control the translation and rotation stages, for example, to coordinate motion between the workpiece 102, the mask 130 and the laser 110. The controller 150 may be programmed such that the mask 130 and the workpiece 102 perform interpolated moves in opposing directions with the magnitude of mask movement being larger by a scale factor equal to the demagnification. Thus, the controller 150 controls opposing motion to cause the laser image 118 to precisely track the position of the moving workpiece 102, i.e., remaining at the same position relative to the workpiece 102 as different areas of the mask 130 are exposed.

The controller 150 may also control precision laser triggering, for example, using a fire on the fly technique. Controlling the precision laser triggering allows the depth of the process to be varied. Control of the coordinated motion together with control of the laser triggering thus controls the power density and the geometry of the 3-D structure being machined.

Thus, the machining system and method, consistent with embodiments of the present invention, uses coordinated opposing motion (COMO) and/or convolution of intensity techniques to create a 3-D structure on the rotating workpiece 102. Consistent with one embodiment of the present invention, a method of machining includes rotating a workpiece about an axis of rotation, translating the workpiece in a first direction along the axis of rotation, translating a mask defining a shape in a second direction opposite the first direction, and directing a laser beam at the mask such that the laser beam is scanned across the mask and at least a portion of the laser beam passes through the mask and toward the workpiece. The method further includes coordinating opposing motion of the mask and the workpiece to cause the laser beam to be imaged onto the workpiece with a shape corresponding to the shape defined by the mask. Rotation of the workpiece and the shape of the laser beam imaged on the workpiece produce different vectorial intensities on the workpiece such that material of the workpiece is removed to different respective depths to form a three-dimensional structure.

Consistent with another embodiment of the present invention, a system of machining includes a workpiece holder configured to rotate a workpiece about an axis of rotation and configured to translate the workpiece in a first direction along the axis of rotation. The system also includes a laser configured to generate a laser beam, and a beam delivery system configured to deliver the laser beam from the laser toward the workpiece. A mask defining a shape is configured to pass at least a portion of the laser beam in the shape, and a mask stage is configured to translate the mask in a second direction generally opposite the first direction. A controller coordinates motion of the mask with motion of the workpiece.

Consistent with a further embodiment of the present invention, a method of machining includes: rotating a workpiece about an axis of rotation; generating a shaped laser beam that is longer in a first axis than a second axis; moving a mask defining a pattern such that the shaped laser beam scans the mask to produce a laser beam image; demagnifying the laser beam image to produce a demagnified laser beam image; and imaging the demagnified laser beam image onto the workpiece as the workpiece rotates.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A method of machining comprising:
   rotating a workpiece about an axis of rotation;
   translating said workpiece in a first direction along said axis of rotation;
   translating a mask in a second direction opposite said first direction, said mask defining at least one shape;
   directing a laser beam at said mask such that said laser beam is scanned across said mask and at least a portion of said laser beam passes through said mask and toward said workpiece; and
   coordinating opposing motion of said mask and said workpiece to cause said laser beam to be imaged onto said workpiece with a shape corresponding to said shape defined by said mask, wherein rotation of said workpiece and said shape of said laser beam imaged on said workpiece produce different vectorial intensities on said workpiece such that material of said workpiece is removed to different respective depths to form a three-dimensional structure.

2. The method of claim 1 wherein said workpiece is generally cylindrical in shape.

3. The method of claim 1 wherein said laser beam is a shaped laser beam that is longer in a first axis than a second axis, and wherein said mask is translated such that said shaped laser beam scans said mask in a direction of said second axis.

4. The method of claim 1 wherein directing said beam includes demagnifying said beam such that said shape imaged onto said workpiece is smaller than said shape on said mask.

5. The method of claim 1 wherein said laser beam is imaged onto a top surface of said workpiece.

6. The method of claim 1 wherein said laser beam is imaged onto a tangential surface of said workpiece.

7. The method of claim 1 wherein the vectorial intensities on the workpiece vary such that the vectorial intensities are higher when the shape of the beam imaged on the workpiece is wider in the direction of rotation.

8. The method of claim 1 wherein said mask includes at least one aperture having a shape including a V-shaped portion such that the vectorial intensities increase from a tip of the V-shaped portion to a wider portion of the V-shaped portion causing an increasing amount of material to be removed from the tip to the wider portion.

9. The method of claim 1 wherein rotating and translating the workpiece include engaging each end of the workpiece.

10. The method of claim 8 wherein the workpiece is placed under tension while rotating and translating.

11. The method of claim 8 wherein the workpiece is rotated with substantially no rotational torque transferred to the workpiece.

* * * * *